US008252722B2

(12) United States Patent  (10) Patent No.: US 8,252,722 B2
Stoller  (45) Date of Patent: Aug. 28, 2012

(54) CONTROLLING PLANT PATHOGENS AND PESTS WITH APPLIED OR INDUCED AUXINS (75) Inventor: Jerry H. Stoller, Houston, TX (US)

(73) Assignee: Stoller Enterprises, Inc., Houston, TX (US)

( * ) Notice: Subject to any disclaimer, the term of this patent is extended or adjusted under 35 U.S.C. 154(b) by 696 days.

(21) Appl. No.: 10/677,708

(22) Filed: Oct. 2, 2003

(65) Prior Publication Data

US 2005/0043177 A1 Feb. 24, 2005

(51) Int. Cl.
A01N 43/36 (2006.01)
(52) U.S. Cl. ....................................... 504/138
(58) Field of Classification Search ................. 504/101; 514/266, 419, 450, 468, 557, 570, 573, 762
See application file for complete search history.

(56) References Cited

U.S. PATENT DOCUMENTS

| 4,286,020 A | * | 8/1981 | Himel et al. | 428/407 |
| 4,496,388 A | * | 1/1985 | Clough | 504/272 |
| 4,675,327 A | * | 6/1987 | Fredrick | 514/383 |
| 4,755,397 A | * | 7/1988 | Eden et al. | 427/213.3 |
| 5,188,655 A | | 2/1993 | Jones et al. | |
| 6,361,999 B1 | | 3/2002 | Lin et al. | |
| 6,399,646 B1 | | 6/2002 | Riggle | |
| 2005/0197253 A1 | | 9/2005 | Stoller et al. | |
| 2005/0198896 A1 | | 9/2005 | Quaghebeur | |

FOREIGN PATENT DOCUMENTS

| AU | 716534 | | 2/2000 |
| BR | PI9906202 | | 9/2001 |
| CN | 1116044 | | 2/1996 |
| CN | 1262037 A | * | 8/2000 |
| CN | 1391807 | | 1/2003 |
| DE | 4138209 | | 5/1993 |
| DE | 4339198 | | 5/1995 |
| DE | 19746366 | | 5/1999 |
| EP | 0935918 | | 8/1999 |
| GB | 1565906 | * | 4/1980 |
| JP | 51001209 | | 1/1976 |
| JP | 57118503 | | 7/1982 |
| JP | 07242590 | | 9/1995 |
| JP | 95102367.5 | * | 2/1996 |
| JP | 2002262687 | | 9/2002 |
| JP | 02117261.7 | * | 1/2003 |
| WO | 8703780 | | 7/1987 |
| WO | 9118512 | | 12/1991 |
| WO | 9400986 | | 1/1994 |
| WO | WO 9400986 | * | 1/1994 |
| WO | 9503702 | | 2/1995 |
| WO | 9628026 | | 9/1996 |
| WO | 9800023 | | 1/1998 |
| WO | 99/49728 | | 10/1999 |
| WO | 00/05954 | | 2/2000 |
| WO | 03096806 | | 11/2003 |
| WO | WO2005/021715 A2 | | 3/2005 |

OTHER PUBLICATIONS

Abstract of CN 1262037A, Aug. 9, 2000.*
Ogbonna et al (Effect of seed-pretreatment with some plant growth regulators on germination, growth and yield of cowpea, Nippon Sakumotsu Gakkai Kiji, 1989, 58(4), 641-7). ABS.*
Prasad et al (Physio Therapy of Rice Plant against the root-knot nematode meloidogyne-graminicola, Biological Sciences, 1976,vol. 42 No. 6, pp. 295-298). ABS.*
European Supplementary Search Report of corresponding application No. 04781404.1 dated Mar. 31, 2010.
English translation of DE 19746366 in the Name of Temmen GmbH.
English translation of DE 4138209 in the Name of Seifert, et al.
English translation of DE 4339198 in the Name of Max Planck Gesellschaft.
English translation of BR PI9906202 in the Name of Unicamp Universidade Estadual de Campinas Unicamp.
English translation of CN 1116044 in the Name of Huaibei Coal Normal College.
English translation of CN 1391807 in the Name of Sichuan Lomon Fusheng Technology Co., Ltd.
English translation of JP 51001209 in the Name of Sasano.
English translation of JP 57118503 in the Name of Sumitomo Chemical Co.
English translation of JP 07242590 in the Name of Sumitomo Chemcial Co.
English translation of JP 2002262687 in the Name of Nettai Rin Saisei Gijutsu Kenkyu Kumiai.
English translation of WO 95/03702 in the Name of Consejo Superior Investigaciones Cientificas.
Jarvis, B.C. et al. "Auxin and Boron in Relation to the Rooting Response and Ageing of Mung Bean Cuttings." New Phytologist (1983), vol. 95, pp. 509-518.
Jarvis, B.C. et al. "The Interaction Between Auxin and Boron in Adventitious Root Development." New Phytologist (1984), vol. 97, pp. 197-204.
International Preliminary Report on Patentability for PCT/US04/26700, dated Jun. 16, 2006.
Written Opinion of the International Searching Authority for PCT/US04/26700, dated Jan. 4, 2006.
International Search Report for PCT/US04/26700, dated Jan. 4, 2006.
International Preliminary Report on Patentability for PCT/US04/26851, dated Jun. 16, 2006.
Written Opinion of the International Searching Authority for PCT/US04/26851, dated Dec. 12, 2005.
International Search Report for PCT/US04/26851, dated Dec. 12, 2005.
U.S. Appl. No. 10/920,487, filed Aug. 18, 2004.
Bernier, et al. Physiological Signals That Induce Flowering. The Plant Cell, Oct. 1993, vol. 5, p. 1147-1155. American Society of Plant Physiologists.
Coenen, et al. Auxin-cytokinin Intersections in Higher Plants: Old Problems and New Tools. Trends in Plant Science, Sep. 1997, vol. 2(9) p. 351-356. Elsevier Science Ltd.

(Continued)

Primary Examiner — Alton Pryor
(74) Attorney, Agent, or Firm — Gary L. Bush; Andrews Kurth LLP (57) ABSTRACT The present invention is directed to methods for inhibiting the growth of disease organisms, particularly fungi and bacteria, on plant tissues. The present invention is also directed to methods for inhibiting the infestation of plants by insects and larva, particularly sucking and chewing insects. These methods are achieved by applying an auxin or a plant growth regulator (PGR) which will effect the level of auxin in the plant tissue to the seeds or tubers of the plant prior to planting or to the roots, foliage, flowers or fruit of the plant after planting.

7 Claims, 4 Drawing Sheets

OTHER PUBLICATIONS

Kirillova I.G., et al. Effects of Ambiol and 2-chlorethylphosphonic Acid on the Contents of Phytohormones in Potato Leaves and Tubers. Mar. 2003. Prikladnaya Biokhimiya I Mikrobiologiya, vol. 39, No. 2, pp. 237-241. Orel State University [ABS].

Mohr, et al. Physiology of Hormone Action, Chapter 23 in Plant Physiology. Springer 1995, p. 383-408.

Nath et al. Propagation of Certain Bamboo Species From Chemically Treated Culm Cuttings, Indian Journal of Forestry, 1986, vol. 9 No. 2, pp. 151-156.

Ono, E.O., Rodrigues, J.D., and do Pinho, S.Z. Interactions Between Auxins and Boric Acid in the Rooting of Stem Cuttings of *Coffea arabica* L. CV Mundo Novo. Scientia Agricol (Piracicaba, Brazil), 1992, vol. 49 (Numero Espec.), 23-27.

Ono, E.O., Niimachi, Pilott, J.D., and of Pinho, S.Z. Interactions Between Auxins and Boric Acid in the Rooting of Stem Cuttings of *Coffea arabica* L. CV Mundo Novo. Scientia Agricol (Piracicaba, Brazil), 1992, vol. 49 (Numero Espec.).

Ono, E.O., Rodrigues, J.D., Rodgues, S.D. Interactions Between Auxins and Boron in the Rooting of Camellia Japonica Cuttings. Revista Brasileira de Fisiologia Vegetal. 1992, vol. 4(2):107-112.

Romanov, et al. Effect of Indole-3-acetic acid and Kinetin on Tuberisation Parameters of Different Cultivars and Transgenic Lines of Potato in vitro. Plant Growth Regulation, vol. 32, No. 2-3, Nov. 2000, pp. 245-251. Kluwer Academic Publishers.

Trifu et al. The Effect of the Complex Treatment With Cobalt-60 Emitted Gamma Rays, Beta Indoleacetic Acid (IAA) and Boron on RNA Dynamics in Corn, Contributii Botanice, 1977, 183-189.

Trifu et al. The Effect of the Complex Treatment With Cobalt-60 Emitted Gamma Rays, Beta Indoleacetic Acid (IAA) and Boron on RNA Dynamics in Corn, Contributii Botanice, 1977, 183-189. [English Abstract only].

Cohen, et al. Local and Systemic Protection Against Phytophthora Infestans Induced in Potato and Tomato Plants by Jasmonic Acid and Jasmonic Methyl Ester. Phytopathology, St. Paul, MN vol. 83, No. 10, Jan. 1, 1993, pp. 1054-1062.

Penninckx, et al. Pathogen-Induced Systemic Activation of a Plant Defensin Gene in Arabidopsis Follows a Salicylic Acid-Independent Pathway Plant Cell. American Society of Plant Physiologists, Rockville, MD vol. 8, No 12, Dec. 1, 1996, pp. 2309-2323.

Xu, et al. Plant Defense Genes are Synergistically Induced by Ethylene and Methyl Jasmonate. Plant Cell, American Society of Plant Physiologists, Rockville, MD vol. 6. No. 8, Aug. 1, 1994, pp. 1077-1085.

\* cited by examiner

FIG. 2

CONTROLLING PLANT PATHOGENS AND PESTS WITH APPLIED OR INDUCED AUXINS

BACKGROUND OF THE INVENTION

I. Field of the Invention

The present invention generally relates to methods for improving the resistance of plants to attack by disease organisms without adversely effecting plant growth. More specifically, the present invention is directed to methods for improving the resistance of plants to attack by disease organisms including fungi, bacteria and insects by applying an effective amount of an auxin or of another plant growth regulator which will affect the level of auxin in the plant tissue.

II. Description of the Background

Agricultural pesticides are used to control unwanted fungi, bacteria and insect populations. These compounds have allowed the commercial grower to manage the continual attack on his crops by these disease organisms and insects. Similarly, the homeowner and casual gardener have been able to control these pests. Although these traditional chemical applications have been valuable in the past, as environmental concerns have increased, it is unlikely that commercial growers will be able to continue to use pesticides at the same rates in the future. Therefore, improved methods for controlling disease and insect attack by augmenting and stimulating the plant's natural processes of protection are desirable.

Plant hormones have been known and studied for years. Plant hormones may be assigned to one of five categories: auxins, cytokinins, gibberellins, abscisic acid and ethylene. Ethylene has long been associated with fruit ripening and leaf abscission. Abscisic acid causes the formation of winter buds, triggers seed dormancy, controls the opening and closing of stomata and induces leaf senescence. Gibberellins, primarily gibberellic acid, are involved in breaking dormancy in seeds and in the stimulation of cell elongation in stems. Gibberellins are also known to cause dwarf plants to elongate to normal size. Cytokinins, e.g., zeatin, are produced primarily in the roots of plants. Cytokinins stimulate growth of lateral buds lower on the stem, promote cell division and leaf expansion and retard plant aging. Cytokinins also enhance auxin levels by creating new growth from menstematic tissues in which auxins are synthesized. Auxins, primarily indole-3-acetic acid (IAA) promote both cell division and cell elongation, and maintain apical dominance. Auxins also stimulate secondary growth in the vascular cambium, induce the formation of adventitious roots and promote fruit growth.

Auxins and cytokinins have complex interactions. It is known that the ratio of auxin to cytokinin will control the differentiation of cells in tissue cultures. Auxin is synthesized in the shoot apex, while cytokinin is synthesized mostly in the root apex. Thus, the ratio of auxin to cytokinin is normally high in the shoots, while it is low in the roots. If the ratio of auxin to cytokinin is altered by increasing the relative amount of auxin, root growth is stimulated. On the other hand, if the ratio of auxin to cytokinin is altered by increasing the relative amount of cytokinin, shoot growth is stimulated.

The most common naturally occurring auxin is indole-3-acetic acid (IAA). However, other synthetic auxins, including indole-3-butyric acid (IBA); naphthalene acetic acid (NAA); 2,4-dichlorophenoxy acetic acid (2,4-D); and 2,4,5-trichlorophenoxy acetic acid (2,4,5-T or agent orange) are known. While these are recognized as synthetic auxins, it should be acknowledged that IBA does naturally occur in plant tissues. Many of these synthetic auxins have been employed for decades as herbicides, producing accelerated and exaggerated plant growth followed by plant death. Agent orange gained widespread recognition when it was used extensively by the United States Army and Air Force in deforestation applications during the Vietnam War. 2,4-D finds continuing use in a number of commercial herbicides sold for use by the home gardener.

Compounds are classified as auxins based on their biological activity in plants. A primary activity for classification includes simulation of cell growth and elongation. Auxins have been studied since the 1800's. Charles Darwin noticed that grass coleoptiles would grow toward a unidirectional light source. He discovered that the growth response of bending toward the light source occurred in the growth zone below the plant tip, even though it was the tip that perceived the light stimulus. Darwin suggested that a chemical messenger was transported between the plant tip and the growth zone. That messenger was later identified as an auxin.

All plants require a certain ratio of auxin, i.e., IAA, to cytokinin for cell division. While the ratios may vary, it is well known that the ratio of IAA to cytokinin must be much greater for cell division in the apical meristem tissue than the ratio in the meristem tissue of the roots. Each part of a plant may require a different IAA to cytokinin ratio for cell division. For example, different ratios may be required for cell division in the stem, fruit, grain and other plant parts. In fact, it has been estimated that the ratio for apical meristem cell division may be considerably more, in fact, as much as 1000 times greater than the ratio necessary for root cell division. While the mechanism by which this ratio is determined remains unknown, other hormones and enzymes are likely to be involved in its perception.

Plants are most able to resist attack by disease and insects when growing at temperatures from about 68° F. to about 87° F. (about 21-30° C.). In this temperature range it is presumed that plants produce sufficient amounts of auxins, particularly IAA, to maintain normal growth. While ideal temperatures vary among species, crop pants typically grow best in the foregoing range. While temperature is an important factor, it should also be noted that other environmental factors can effect cell division. The moisture content of the plant, the nutrient status (especially the level of available nitrogen), the light intensity on the plant and the age of the plant, together with the temperature, all effect the ability of the plant to produce plant hormones, including IAA and cytokinin which dictate cell division.

As the temperature rises about 90° F. (about 31° C.) or falls below about 68° F. (21° C.) plant growth and cell division slow. Further, susceptibility to attack by disease organisms, including fungi, bacteria and insects, increases. As the temperature further increases above about 90° F. and drops below about 68° F., the production of IAA and other plant hormones decreases at an accelerating rate. Thus, it becomes difficult, if not impossible, to achieve new cell growth at temperatures above about 100° F. Similarly cell growth slows and then ceases as temperatures plunge significantly below about 680 F.

During normal growing conditions with adequate moisture and temperature, i.e., temperatures between about 70° F. and 90° F., the plants will produce an abundance of IAA. The high ratio of IAA to cytokinin and the presence of other hormones inhibit proper cell division in disease microorganisms. Cell division may be further impeded by other inhibitive compounds produced by IAA and other plant hormones. As temperatures increase above about 90° F. or below about 68° F., the ability of plants to produce IAA rapidly diminishes. It is presumed that as IAA production decreases the ratio of IAA to cytokinin decreases to a level where some or all of these microorganisms may multiply and feed in and on the host plant. It should be understood that different microorganisms will require different ratios of IAA to cytokinin to stimulate cell division. Thus, it should be expected that pathological organisms feeding on plant roots require a lower IAA to cytokinin ratio than organisms feeding on the upper parts of the plant. Thus, microorganisms requiring greater levels of IAA may attack the upper plant tissues, e.g., the apical meristem and leaf tissue, where higher IAA levels exist. Similarly, disease organisms requiring lower IAA levels, e.g., soil borne root diseases, may attack the roots where lower IAA levels exist.

When plants are rapidly growing under conditions which include ample moisture, ideal temperatures and ample amounts of nitrogen fertilizer, auxins are efficiently transported out of the tissues where they are metabolized and move downward in the plant. This results in the redistribution of auxin and the reduction of the auxin level in the tissues where it was produced. The result is tissues which are deficient in the level of auxin. These tissues, now dominated by gibberellins, are very susceptible to attack by disease and insects.

All plant diseases are caused by microorganisms. The major microorganisms effecting plant pathological problems are fungi and bacteria. These microorganisms, like the plant, require a certain amount of IAA to carry on cell division. Different microorganisms, like plants, require different amounts of IAA for cell division. Those differences might explain why different microorganisms attack different species of plants and attack different parts of those plants. Such specific attacks may be intended to provide the microorganism with the proper level of IAA to stimulate rapid cell division by feeding on a host plant or portion thereof having the desired IAA concentration. Thus, resistance to such disease organisms may be improved, if the ratio of IAA to cytokinin and other hormones is increased beyond a level sought by the disease organism. Such an increase may be obtained by providing the plant with additional auxin.

By controlling the level of auxins, most often IAA, in plant tissues, the ability of plants to resist attack by both pathogens and pests can be increased. Plant diseases may be controlled by applying to stressed plants additional auxin or other hormones which will affect the auxin level in the tissues. Alternatively, the same results can be achieved by application of other plant hormones which will affect the auxin level in the tissues. For example, the application of cytokinin or other hormones has an affect on regulating the production and/or transport of auxins within the plant. Thus, the application of other plant growth regulators, e.g., cytokinin, can be used to manipulate the level of auxin in the plant. Thus, disease and insect control can be achieved by application of naturally occurring or synthetic auxins or other hormones which will affect the auxin levels without requiring the use of environmentally harmful pesticides.

Those skilled in the art have long sought environmentally friendly methods for improving plant resistance to disease organisms, including both plant pathogens, e.g., fungi and bacteria, and pests, e.g., insects and their larvae. Thus, there has been a long felt, but unfulfilled need for such methods. The present invention solves that need.

SUMMARY OF THE INVENTION

The present invention is directed to methods for inhibiting the attack of disease organisms on and in plant tissues. Such organisms may include both plant pathogens, e.g., fungi and bacteria, and pests, e.g., insects and their larvae, including both sucking and chewing insects.

In the methods of the present invention, an auxin in an amount effective to inhibit growth of such organisms, both plant pathogens and pests, is applied to the plant tissue. However, the auxin is applied in an amount insufficient to negatively effect growth of the plant tissues. Alternatively, other plant growth regulators (PGRs) which act by altering the level or effectiveness of endogenous or applied auxin may be used.

The auxin is selected from the group consisting of the natural auxins, synthetic auxins, auxin metabolites, auxin precursors, auxin derivatives and mixtures thereof. The preferred auxin is a natural auxin, most preferably indole-3-acetic acid. The presently preferred synthetic auxin is indole-3-butyric acid. Alternatively, manipulation of the auxin level within the desired range can be achieved by application of a plant growth regulator or hormone, e.g., cytokinin or gibberellic acid.

In the methods of the present invention the auxin or PGR is applied to the seed or tubers for the plant prior to planting. Alternatively, the auxin or PGR is applied to the roots, foliage, flowers or fruits of the plant after planting. When applied to the seed or tubers, auxin is preferably applied at a rate of about 0.0028 to about 0.028 grams auxin per 100 kg. seed weight. When applied to potato seed pieces, the rate of application may be calculated so as to result in about 0.0125 to about 2.8 grams auxin per hectare of planted pieces. When applied to the roots, foliage, flowers or fruits of plants, the auxin should be applied at a rate of about 0.0002 to about 0.06 grams auxin per hectare per day. Multiple applications may be required over an extended growing period.

The auxin or PGR may be applied as an aqueous solution or as a powder. When applied as an aqueous solution, the solution may be applied to the plant tissue by conventional spraying or irrigation techniques. The solution may further include a metal selected from the group consisting of the alkaline earth metals, transition metals and mixtures thereof. Such metals preferable are selected from the group consisting of calcium, zinc, copper, manganese and mixtures thereof. Seeds or tubers may be treated prior to planting by spraying with or by immersion in such aqueous solutions.

Auxins and PGRs may also be applied as a dry powder. In such applications, the auxin or PGR is mixed with an environmentally and biologically compatible material. The powder may be applied to the foliage, flowers or fruits of the plant by conventional dusting methods. Alternatively, the powder may be encapsulated in a biologically compatible material to provide slow release when placed on or near the seeds, tubers or roots of the plant. Exemplary biologically compatible materials include the clays, lignites, resins, silicones and mixtures thereof.

The methods of the present invention include inhibiting the growth of disease organisms, e.g., bacteria and fungi, by applying an effective amount of auxin or PGR to the plant tissue. Fungi whose growth may be inhibited by these methods include, without limitation, those selected from the families including *Fusarium, Rhizoctonia, Pythium* and *Phytophthora*. Bacteria which may be controlled by these methods include, without limitation, *Erwinia* and *Pseudomonas*. Insects controlled or inhibited by application of auxin include, without limitation, both the sucking insects and chewing insects. Examples of sucking insects include mites, aphids, thrips, white fly, leaf hoppers, flea hoppers and scaling insects. Examples of chewing insects include *Lepidoptera* and *Helidoceras*.

Finally, the present invention includes seeds and seed pieces for producing plants having dispersed on the surface thereof an auxin in an amount effective to inhibit growth of harmful organisms in or on tissues of the plant, but in an amount insufficient to negatively effect growth of the plant tissues. Alternatively, a plant growth regulator, e.g., a plant hormone such as cytokinin or gibberellic acid, which acts by effecting the level or effectiveness or applied auxin may be used. Such PGR should be dispersed on the surface of seeds or seed pieces in an amount effective to manipulate the auxin level within the desired range.

The methods of the present invention have been found to significantly increase the resistance of plants to attack by disease organisms and insects. Significantly, the increased resistance to disease and insect attack is achieved without the use of environmentally hazardous fungicides and insecticides. The methods of the present invention improve the resistance of plants to attack by disease organisms and insects by applying naturally occurring or synthetic auxins or other plant hormones which act by modulating the level or effectiveness of endogenous or applied auxins in an environmentally safe process. Thus, the long felt, but unfulfilled need for environmentally friendly methods for enhancing resistance of plants to disease and insect attack have been met. These and other meritorious features and advantages of the present invention will be more fully appreciated from the following detailed description and claims.

BRIEF DESCRIPTION OF THE DRAWINGS

Other features and intended advantages of the present invention will be more readily apparent by reference to the following description in connection with the accompanying drawings wherein.

While the invention will be described in connection with the presently preferred embodiments, it will be understood that it is not intended to limit the invention to those embodiments. To the contrary, it is intended to cover all alternatives, modifications and equivalents as may be included in the spirit of the invention as defined in the appended claims.

DETAILED DESCRIPTION OF THE INVENTION

The present invention is directed to methods for inhibiting the growth of pathogens on and in plant tissues and the infestation of plants by pests, including insects and their larvae. Exemplary pathogens which may be inhibited by the methods of the present invention include diseases caused by the growth of fungi and bacteria. Pests which may be controlled using the methods of the present invention include both sucking and chewing insects.

In the methods of the present invention, an auxin in an amount effective to inhibit growth of disease causing organisms, either pathogens or pests, is applied to the plant tissue. While the auxin is applied in an amount sufficient to inhibit growth of such organisms, it must be applied in an amount insufficient to negatively affect growth of plant tissue. Alternatively, the level or effectiveness of endogenous or applied auxin may be manipulated to fall within those ranges. Such manipulation can be achieved by applying other plant growth regulators (PGRs), e.g., plant hormones such as cytokinin and gibberellic acid, in effective amounts.

Auxins useful in the methods of the present invention are selected from the group consisting of the natural auxins, synthetic auxins, auxin metabolites, auxin pre-cursors, auxin derivatives and mixtures thereof. The preferred auxin is indole-3-acetic acid (IAA), a natural auxin. The preferred synthetic auxin is indole-3-butyric acid (IBA). Other exemplary synthetic auxins which may be employed in the methods of the present invention include indole propionic acid, indole-3-butyric acid, phenylacetic acid, naphthalene acetic acid (NAA), 2,4-dichlorophenoxy acetic acid, 4-chloroindole-3-acetic acid, 2,4,5-trichlorophenoxy acetic acid, 2-methyl-4-chlorophenoxy acetic acid, 2,3,6-trichlorobenzoic acid, 2,4,6-trichlorobenzoic acid, 4-amino-3,4,5-trichloropicolinic acid and mixtures thereof. Other plant growth hormones which act by altering the level or effectiveness of endogenous or applied auxin within the plant tissue may also be applied. These hormones (PGRs) may include ethylene, cytokinins, gibberellins, abscisic acid, brassinosteroids, jasmonates, salicylic acids and precursors and derivatives thereof.

In the methods of the present invention, the auxin or PGR is applied to the seeds or tubers of the plant prior to planting. Alternatively, the auxin or PGR is applied to the roots, foliage, flowers or fruits of a plant after planting. When applied to the seeds or tubers, e.g., to bean seeds or potato pieces, respectively, the auxin should be applied at a rate of about 0.0028 to about 0.028 grams auxin per 100 kg seed weight. In a more preferred embodiment, the auxin is applied to seeds, e.g., bean seeds, at a rate of about 0.016 to about 0.112 grams auxin per 100 kg seed weight. On the other hand, when applied to potato seed pieces, the auxins should be applied at a rate to result in about 0.125 to about 2.8 grams auxin per hectare of planted seed pieces. In a more preferred embodiment, the rate of application to potato seed pieces should result in about 0.125 to about 0.28 grams auxin per hectare of planted seed pieces. When applied to the roots, foliage, flowers or fruits of plants, the auxin should be applied at a rate of about 0.0002 to about 0.06 grams auxin per hectare per day, more preferably at a rate of about 0.002 to about 0.01 grams auxin per hectare per day. Application may be made over a series of days during the growing period based upon perceived stress on the plants and observed infestation. Another PGR should be applied at a rate sufficient to manipulate the level of endogenous and/or applied auxin to within the stated ranges.

The auxin or PGR may be applied as an aqueous solution or as a powder. When applied as an aqueous solution, the solution may include a metal selected from the group consisting of the alkaline earth metals, the transition metals and mixtures thereof. Preferred metals include calcium, zinc, copper, manganese and mixtures thereof. Most preferred is calcium. When included, the metal may be present in a range from about 0.001 to about 5.0 percent-by-weight.

When applied as an aqueous solution, the auxin or PGR containing solution may be sprayed on seeds or tubers using conventional spray equipment. Alternatively, the seeds or tubers may be immersed in an aqueous solution of the auxin.

When applied to the roots, foliage, flowers or fruits of plants, an aqueous solution containing the auxin or PGR may be applied using conventional irrigation or spray equipment. Alternatively, the auxin or PGR may be applied in a dry form as a powder. When so applied, the auxin or PGR is mixed with a biologically and environmentally compatible material. Such a powder may be applied to the foliage, flowers or fruits by conventional dusting equipment.

Alternatively, the powder may be encapsulated in a biologically compatible material to provide for slow release when placed on or near the seeds, tubers or roots of the plant. Such encapsulated materials may be placed directly on the seeds or tubers or may be dispersed within the root zone of the plant where the slowly released auxin may be absorbed by the roots. Exemplary biologically compatible materials useful in encapsulation include the clays, lignites, resins, silicones and mixtures thereof.

The methods of the present invention are useful for inhibiting the growth of disease pathogens, including fungi, bacteria and mixtures thereof. Fungi which may be inhibited by these methods include, without limitation, those selected from the families including *Fusarium, Rhizoctonia, Pythium* and *Phytophthora*. Bacteria which may be controlled by these methods include, without limitation, *Erwinia* and *Pseudomonas*. Pests controlled or inhibited by application of auxin or PGR in accordance with the methods of the present invention include, without limitation, both the sucking insects and chewing insects. Examples of sucking insects include mites, aphids, thrips, white fly, leaf hoppers, flea hoppers and scaling insects. Examples of chewing insects include *Lepidoptera* and *Helidoceras*.

While the methods of the present invention may be used with substantially all plants, they are particularly useful when applied to crop plants, e.g., dry beans, soy beans, onions, potatoes, corn, cotton and the like.

Finally, the present invention includes seeds and seed pieces for producing plants which have been treated in accord with the present invention. Such seed pieces include a plant seed or seed piece having dispersed on the surface thereof an auxin in an amount effective to inhibit growth of harmful organisms in or on tissues of the plant, but in an amount insufficient to negatively affect growth of the plant tissues. Alternatively, such seeds and seed pieces have dispersed on the surface thereof a PGR in an amount sufficient to manipulate the endogenous and/or applied auxin to within the stated ranges. Such seed pieces may be prepared by spraying an aqueous solution of the auxin or PGR onto the surface of seeds or seed pieces. Alternatively, the seeds or seed pieces may be immersed in an aqueous solution of the auxin or PGR.

In the presently preferred embodiment, the auxin is present in an amount of about 0.0028 to about 0.028 grams of auxin per 100 kg seed weight of beans and similar seeds. Where the seed piece is a potato seed piece, the auxin, in the presently preferred embodiment, is present in an amount to result in about 0.0125 to about 2.8 grams auxin per hectare of planted seed pieces.

Following are several examples of use of the methods of the present invention to inhibit the growth of fungi and the infestation of specific insects on treated plants. These examples are provided by way of illustration only and are not intended to limit the scope of the invention in any way.

EXAMPLE 1

In a field experiment, the effect of treatment of seeds with an aqueous solution containing plant growth regulators, including indole-3-acetic acid (IAA), was studied. In this experiment dry bean seeds were treated by application of an aqueous solution containing IAA, IBA, cytokinin, gibberellic acid and optionally calcium. Controls were merely treated with distilled water. Finally, other seeds were treated with an aqueous solution of Derosal, a commercially available fungicide containing carbendazim and thiram as the active ingredients. Finally, seeds were treated with a combination of the foregoing PGR, Derosal and calcium containing solutions. The various treatments are summarized in the left column of Tables I-V.

Figure 1:
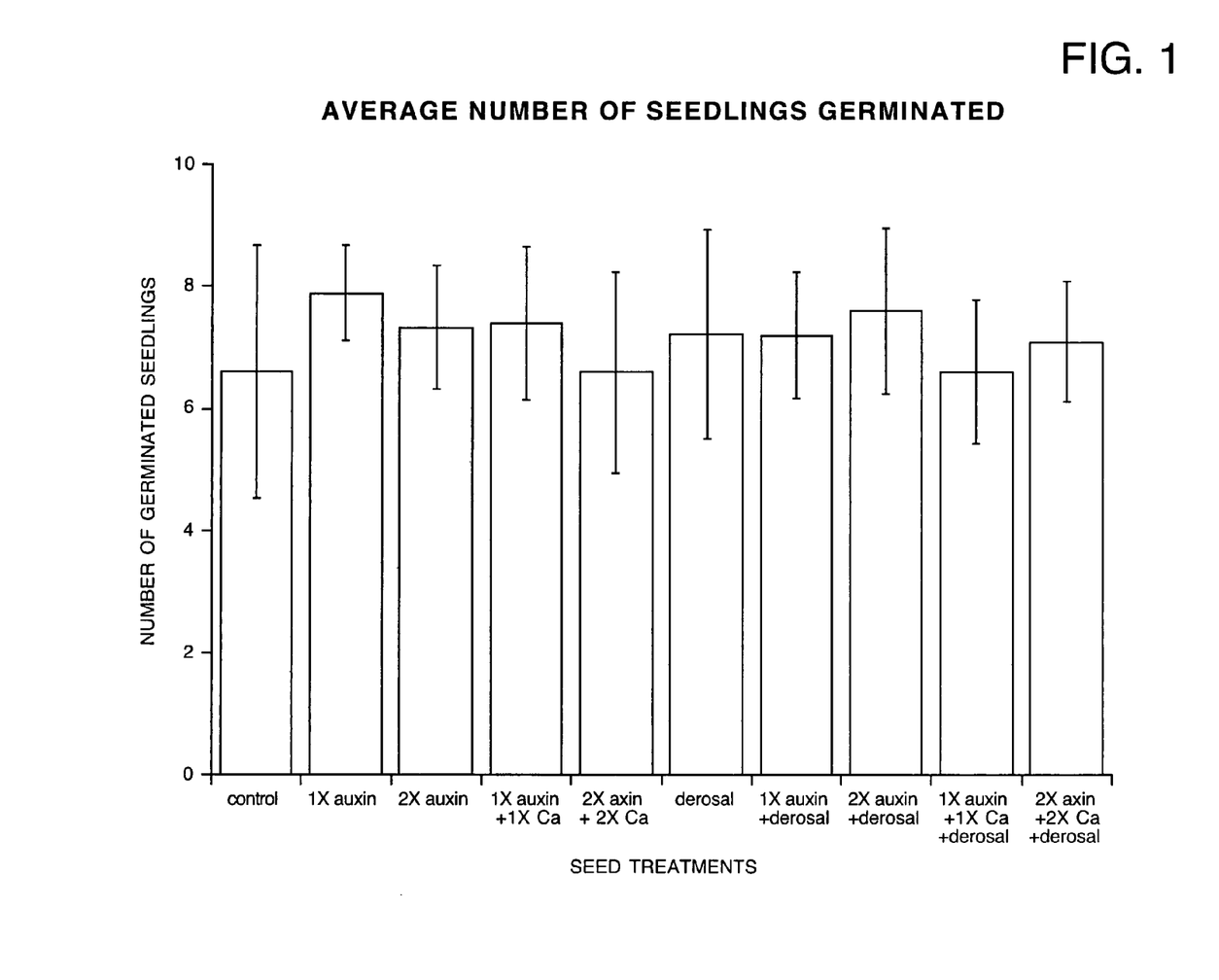
FIG. 1 is a bar graph illustrating germination rates for dry beans treated prior to planting with a conventional fungicide and/or with plant growth regulators, including auxins, in accord with the present invention as summarized in Table I.
Figure 2:
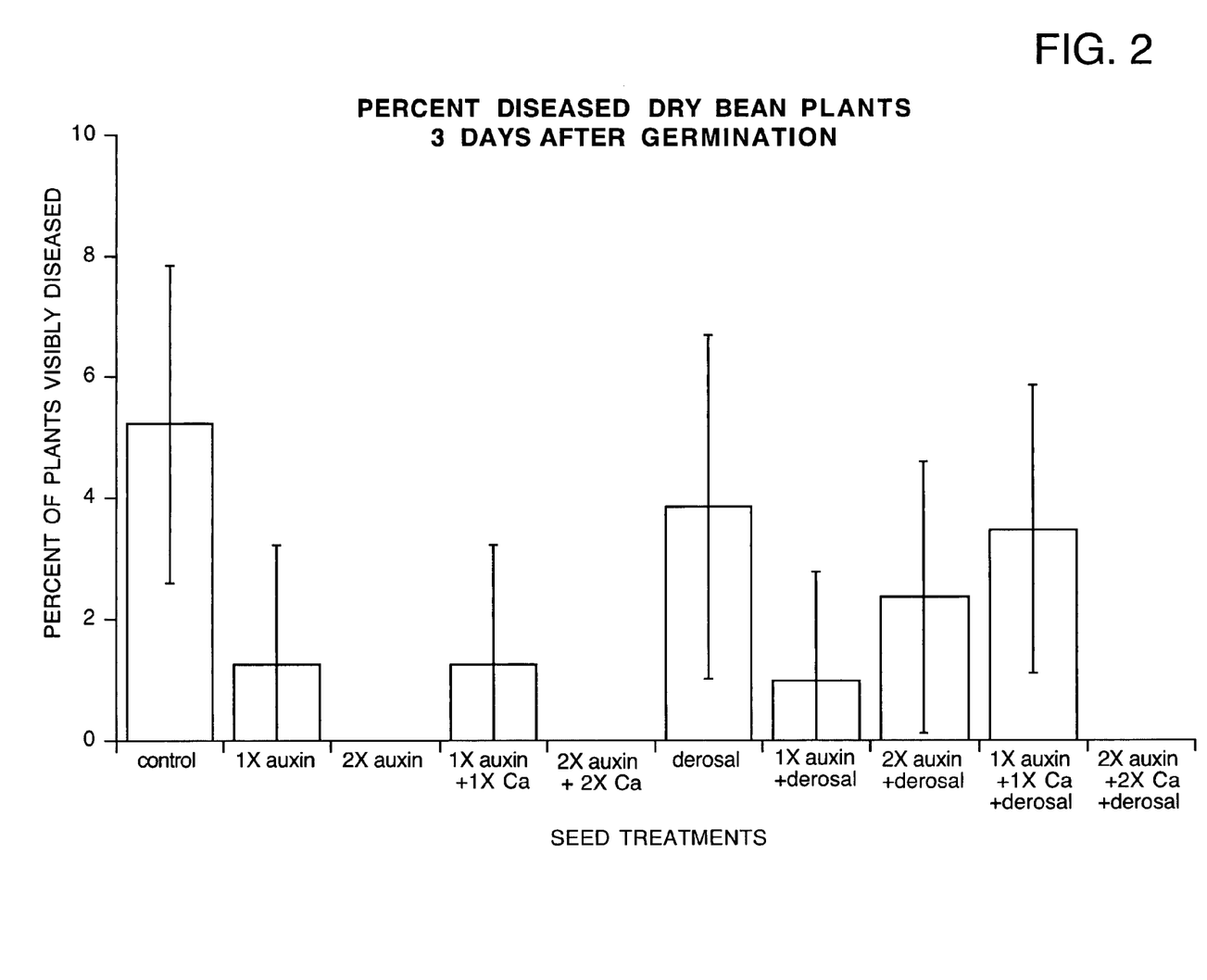
FIG. 2 is a bar graph illustrating the percent of diseased plants observed three (3) days after germination for dry beans treated prior to planting with a conventional fungicide and/or with plant growth regulators, including auxins, in accord with the present invention as summarized in Table II.
Figure 3:
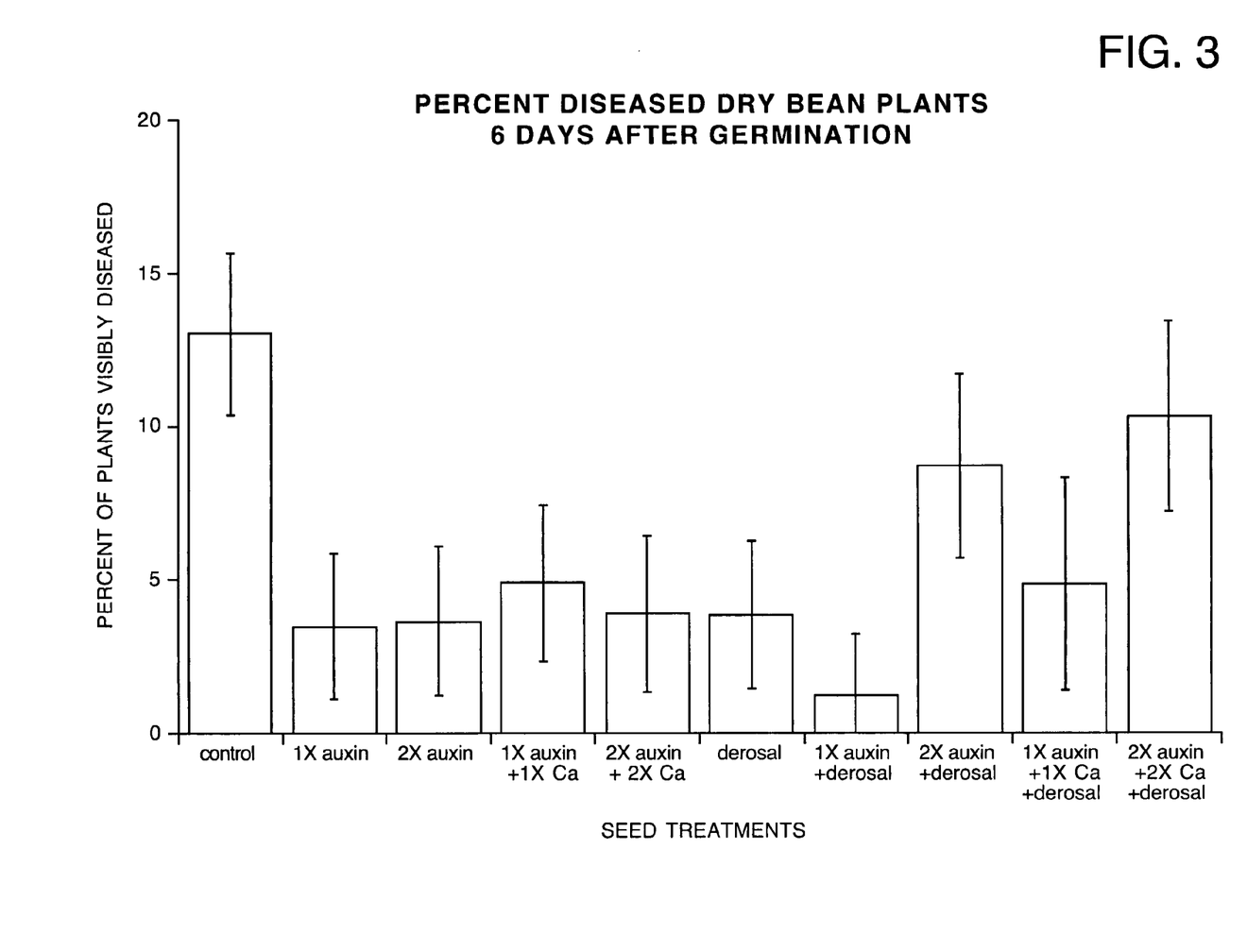
FIG. 3 is a bar graph illustrating the percent of diseased plants observed six (6) days after germination for dry beans treated prior to planting with a conventional fungicide and/or with plant growth regulators, including auxins, in accord with the present invention as summarized in Table III.
Figure 4:
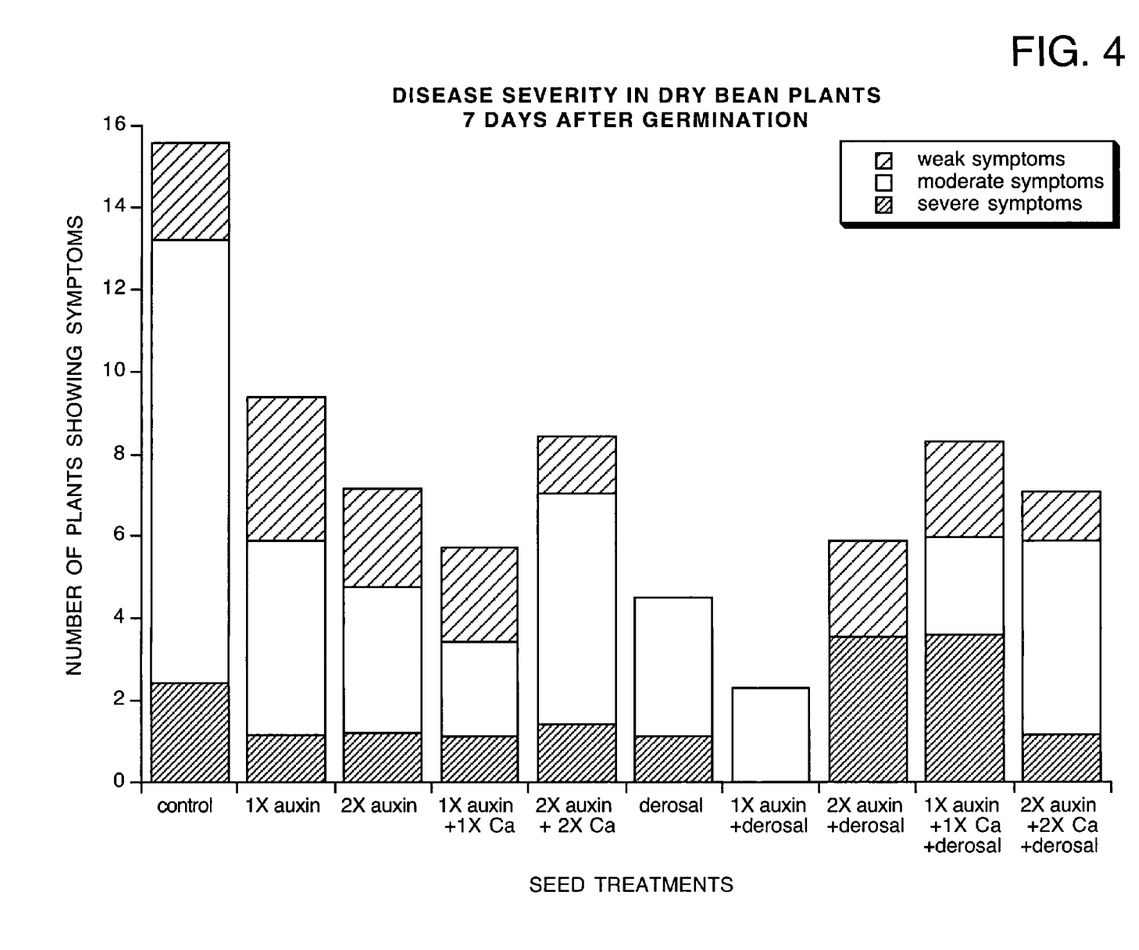
FIG. 4 is a bar graph illustrating the number of diseased plants observed seven (7) days after germination for dry beans treated prior to planting with a conventional fungicide and/or with plant growth regulators, including auxins, in accord with the present invention as summarized in Table IV.

One hundred (100) kg of seeds were treated by spraying with 200, 400 or 600 ml of solutions containing PGR, calcium and/or Derosal in various combinations as listed. Each individual treatment was repeated with ten (10) replications. Nine (9) seeds were planted in each replication. The emerging plants were observed at intervals of 2, 3, 6, 7 and 13 days after germination. Observations are recorded showing the number of plants growing in each replication, together with the number of plants showing signs of disease (*Rhizoctonia solani*) infestation. Finally, the severity of the disease is indicated in the later observations. The results of those observations are summarized in Tables I-IV and are graphically illustrated in FIGS. 1-4.

TABLE I

DRY BEANS - SEEDS TREATED WITH AUXIN-CONTAINING SOLUTIONS
2 days after germination (DAE)

| Treatment | Quantity (ml) | Replications (Number of Seedlings) | | | | | | | | | | Total Plants | Percent Germination |
|---|---|---|---|---|---|---|---|---|---|---|---|---|---|
| | | 1 | 2 | 3 | 4 | 5 | 6 | 7 | 8 | 9 | 10 | | |
| Control | | 7 | 3 | 8 | 9 | 4 | 9 | 7 | 6 | 8 | 5 | 66 | 73.3 |
| PGR Solution | 200 | 9 | 7 | 8 | 8 | 9 | 7 | 8 | 7 | 8 | 3 | 74 | 82.2 |
| PGR Solution | 400 | 8 | 8 | 6 | 8 | 6 | 7 | 7 | 7 | 9 | — | 73 | 81.1 |
| PGR Solution + Ca | 200 + 200 | 9 | 7 | 6 | 6 | 7 | 9 | 8 | 7 | 9 | 6 | 74 | 82.2 |
| PGR Solution + Ca | 400 + 400 | 7 | 6 | 5 | 8 | 8 | 3 | 6 | 7 | 8 | 8 | 66 | 73.3 |
| Derosal | 200 | 8 | 6 | 9 | 5 | 5 | — | 8 | 9 | 6 | 9 | 76 | 84.4 |
| PGR Solution + Derosal | 200 + 200 | 8 | 7 | 8 | 7 | 6 | 9 | 8 | 6 | 6 | 7 | 72 | 80.0 |
| PGR Solution + Derosal | 400 + 200 | 8 | 8 | 7 | 9 | 9 | 9 | 5 | 6 | 7 | 8 | 76 | 84.4 |
| PGR Solution + Ca + Deroral | 200 + 200 + 200 | 8 | 5 | 6 | 8 | 5 | 8 | 7 | 6 | 6 | 7 | 66 | 73.3 |
| PGR Solution + Ca + Derosal | 400 + 400 + 200 | 8 | 6 | 7 | 7 | 7 | 6 | 9 | 8 | 7 | 6 | 71 | 78.9 |

General Information
10 treatments and 10 replications - Randomized entirely
Each replication = 1 vase (bucket) with 9 seeds
No signs of diseases observed.
The PGR Solution comprises an aqueous solution containing 0.015% IAA, 0.005% IBA, 0.009% cytokinin, 0.005% gibberellic acid, 1.000% emulsifier, 0.850% surfactant and 0.050% defoamer.
Calcium, when present, is used in a 10% aqueous solution.
Derosal is a trademark of Bayer Crop Service. Derosal comprises an aqueous solution of carbendazim and thiram.

TABLE II

DRY BEANS - SEEDS TREATED WITH AUXIN-CONTAINING SOLUTIONS
3 days after germination (DAE)

| Treatment | Quantity (ml) | Replications (*Rhizoctonia solani*) No. of Plants/No. of Diseased Plants | | | | | | | | | |
|---|---|---|---|---|---|---|---|---|---|---|---|
| | | 1 | 2 | 3 | 4 | 5 | 6 | 7 | 8 | 9 | 10 |
| Control | | 8 | 6/1 | 9 | 9/1 | 8 | 8/1 | 8 | 8 | 8/1 | 7 |
| PGR Solution | 200 | 9 | 9 | 7 | 8 | 9 | 8 | 9 | 8 | 8 | 8/1 |
| PGR Solution | 400 | 8 | 8 | 9 | 9 | 8 | 7 | 9 | 8 | 8 | 8 |
| PGR Solution + Ca | 200 + 200 | 8 | 7 | 7 | 8/1 | 9 | 9 | 8 | 8 | 8 | 9 |
| PGR Solution + Ca | 400 + 400 | 9 | 6 | 8 | 6 | 9 | 8 | 3 | 9 | 9 | 8 |
| Derosal | 200 | 9 | 9/2 | 9 | 7 | 8/1 | — | 9 | 9 | 9 | 9 |
| PGR Solution + Derosal | 200 + 200 | 10/1 | 8 | 9 | 8 | 9 | 8 | 9 | 7 | 8 | 7 |
| PGR Solution + Derosal | 400 + 200 | 8 | 9 | 8 | 9 | 9/1 | 9 | 7 | 5 | 8 | 8/1 |
| PGR Solution + Ca + Deroral | 200 + 200 + 200 | 8/1 | 8 | 9/1 | 7 | 8 | 9 | 9 | 8 | 9/1 | 8 |
| PGR Solution + Ca + Deroral | 400 + 400 + 200 | 9 | 9 | 9 | 7 | 7 | 9 | 9 | 8 | 8 | 7 |

General Information
10 treatments and 10 replications - Randomized entirely
Each replication = 1 vase (bucket) with 9 seeds
The PGR Solution comprises an aqueous solution containing 0.015% IAA, 0.005% IBA, 0.009% cytokinin, 0.005% gibberellic acid, 1.000% emulsifier, 0.850% surfactant and 0.050% defoamer.
Calcium, when present, is used in a 10% aqueous solution.
Derosal is a trademark of Bayer Crop Service. Derosal comprises an aqueous solution of carbendazim and thiram.

TABLE III

DRY BEANS - SEEDS TREATED WITH AUXIN-CONTAINING SOLUTIONS
6 days after germination (DAE)

| Treatment | Quantity (ml) | Replications (*Rhizoctonia solani*) No. of Plants/No. of Diseased Plants | | | | | | | | | |
|---|---|---|---|---|---|---|---|---|---|---|---|
| | | 1 | 2 | 3 | 4 | 5 | 6 | 7 | 8 | 9 | 10 |
| Control | | 8 | 8/1 | 9/2 | 9/1 | 9/1 | 9/1 | 8 | 7/1 | 8/1 | 8/2 |
| PGR Solution | 200 | 9 | 9 | 7 | 8 | 9/1 | 9/1 | 8 | 9 | 8/1 | 8 |
| PGR Solution | 400 | 8 | 8 | 9 | 8 | 8 | 9/1 | 7/1 | 8 | 9 | 9/1 |
| PGR Solution + Ca | 200 + 200 | 8 | 7/1 | 8/1 | 8 | 9 | 9/1 | 9/1 | 8 | 9 | 8 |
| PGR Solution + Ca | 400 + 400 | 6/1 | 9/1 | 8 | 9/1 | 5 | 8 | 8 | 9 | 9 | 5 |
| Derosal | 200 | 9 | 9 | 9/1 | 9 | 8/1 | — | 9 | 9/1 | 9 | 9 |
| PGR Solution + Derosal | 200 + 200 | 9 | 8 | 9 | 8 | 8 | 9 | 9 | 7 | 8/1 | 9 |
| PGR Solution + Derosal | 400 + 200 | 8/1 | 9 | 9/1 | 9/1 | 9/1 | 8 | 7/2 | 7 | 8/1 | 7 |
| PGR Solution + Ca + Deroral | 200 + 200 + 200 | 8/3 | 8 | 7 | 7 | 8 | 9 | 9/1 | 9 | 8 | 9 |
| PGR Solution + Ca + Deroral | 400 + 400 + 200 | 9/1 | 9/2 | 9/2 | 9/2 | 9 | 7/1 | 8 | 9 | 9/1 | 7 |

General Information
10 treatments and 10 replications - Randomized entirely
Each replication = 1 vase (bucket) with 9 seeds
The PGR Solution comprises an aqueous solution containing 0.015% IAA, 0.005% IBA, 0.009% cytokinin, 0.005% gibberellic acid, 1.000% emulsifier, 0.850% surfactant and 0.050% defoamer.
Calcium, when present, is used in a 10% aqueous solution.
Derosal is a trademark of Bayer Crop Service. Derosal comprises an aqueous solution of carbendazim and thiram.

TABLE IV

DRY BEANS - SEEDS TREATED WITH AUXIN-CONTAINING SOLUTIONS
7 days after germination (DAE)

| Treatment | Quantity (ml) | Replications (*Rhizoctonia solani*) No. of Plants/No. of Diseased Plants | | | | | | | | | | | |
|---|---|---|---|---|---|---|---|---|---|---|---|---|---|
| | | 1 | 2 | 3 | 4 | 5 | 6 | 7 | 8 | 9 | 10 | * | ** |
| Control | | 7/1-1 | 8/1-2 | 8/2-2 | 9/1-1 | 9/1-2 | 9/1-2 | 9/2-2, 3 | 9/1-3 | 8/1-2 | 7/2-2 | 92.2 | 15.7 |
| PGR Solution | 200 | 8 | 9/2-2 | 8/3-1, 2, 3 | 9/1-3 | 8/1-2 | 8/1-3 | 8 | 9 | 9 | 9 | 94.4 | 9.4 |
| PGR Solution | 400 | 8 | 9 | 8/1-3 | 9 | 9/1-1 | 9/1-2 | 7/2-2, 2 | 9 | 8 | 8/1-3 | 93.3 | 7.2 |
| PGR Solution + Ca | 200 + 200 | 9 | 9 | 8 | 9 | 9/2-2, 2 | 9/2-3, 3 | 8 | 8 | 8 | 7/1-1 | 97.8 | 5.7 |
| PGR Solution + Ca | 400 + 400 | 8 | 9 | 9/2-2, 3 | 9 | 5/1-1 | 8 | 6 | 8/1-2 | 6/1-2 | 9/1-2 | 78.9 | 8.4 |
| Derosal | 200 | 9 | 9/1-2 | 9 | 9/1-2 | 9 | 8/1-1 | — | 9 | 9 | 9/1-2 | 98.8 | 5.0 |
| PGR Solution + Derosal | 200 + 200 | 7 | 8/1-2 | 9 | 8 | 8 | 8 | 9 | 9 | 8/1-2 | 9 | 97.8 | 2.3 |

TABLE IV-continued

DRY BEANS - SEEDS TREATED WITH AUXIN-CONTAINING SOLUTIONS
7 days after germination (DAE)

| Treatment | Quantity (ml) | Replications (*Rhizoctonia solani*) No. of Plants/No. of Diseased Plants | | | | | | | | | | * | ** |
|---|---|---|---|---|---|---|---|---|---|---|---|---|---|
| | | 1 | 2 | 3 | 4 | 5 | 6 | 7 | 8 | 9 | 10 | | |
| PGR Solution + Derosal | 400 + 200 | 8 | 8/1-1 | 8/1-1 | 8 | 9/1-1 | 9/1-3 | 8 | 9/1-3 | 9 | 9 | 94.4 | 5.9 |
| PGR Solution + Ca + Deroral | 200 + 200 + 200 | 9 | 9 | 9 | 8/1-3 | 9/1-1 | 7/1-3 | 8 | 8/2-2, 2 | 9/2-1, 1 | 8 | 93.3 | 8.3 |
| PGR Solution + Ca + Derosal | 400 + 400 + 200 | 9 | 8/1-3 | 9 | 8 | 9/1-2 | 7/1-2 | 8 | 9/1-2 | 9/2-1, 2 | 9 | 94.4 | 7.0 |

\* % of germination
\*\* % of diseased plants
The PGR Solution comprises an aqueous solution containing 0.015% IAA, 0.005% IBA, 0.009% cytokinin, 0.005% gibberellic acid, 1.000% emulsifier, 0.850% surfactant and 0.050% defoamer.
Calcium, when present, is used in a 10% aqueous solution.
Derosal is a trademark of Bayer Crop Service. Derosal comprises an aqueous solution of carbendazim and thiram.
x/y-z (x = number of plants, y = number of plants with symptoms and z = disease severity)
Scale of severity
1 = very severe symptoms or dead plants
2 = moderate symptoms (wilted plants)
3 = weak symptoms (initial wilt)

TABLE V

DRY BEANS - SEEDS TREATED WITH AUXIN-CONTAINING SOLUTIONS
13 days after germination (DAE)

| Treatment | Quantity (ml) | Replications (*Rhizoctonia solani*) No. of Plants/No. of Diseased Plants | | | | | | | | | | * | ** |
|---|---|---|---|---|---|---|---|---|---|---|---|---|---|
| | | 1 | 2 | 3 | 4 | 5 | 6 | 7 | 8 | 9 | 10 | | |
| Control | | 7/2-2.5 | 8/4-2 | 8/1-2 | 9/1-1 | 9/5-1.8 | 9/3-1.7 | 8/1-2 | 9/3-2 | 8/2-2.5 | 7/2-2.5 | 91.1 | 26.3 |
| PGR Solution | 200 | 8/2-1.5 | 9/4-2 | 7/2-2.5 | 9/1-2 | 9/1-2 | 9/3-2 | 7/2-2.5 | 8/1-1 | 9/1-2 | 9 | 93.3 | 18.2 |
| PGR Solution | 400 | 8/2-1.5 | 9/1-2 | 9/4-2 | 7 | 9/2-1.5 | 7/3-1.7 | 9/1-1 | 8 | 8/1-2 | 9 | 92.2 | 15.2 |
| PGR Solution + Ca | 200 + 200 | 9 | 9/1-2 | 8/1-2 | 9/1-3 | 9/3-1.7 | 9/4-2 | 7 | 8/1-2 | 8 | 6/1-2 | 91.1 | 13.2 |
| PGR Solution + Ca | 400 + 400 | 8/2-2 | 9-1-2 | 9/2-2.5 | 7 | 5/1-2 | 8 | 6/1-2 | 8/1-2 | 6/1-1 | 9/1-1 | 83.3 | 12.0 |
| Derosal | 200 | 9/1-2 | 9/1-1 | 8/1-3 | 9/2-1.5 | 9/1-3 | 8/2-1.5 | 9/1-2 | 9/1-2 | 9 | 9/1 | 97.8 | 11.2 |
| PGR Solution + Derosal | 200 + 200 | 7/1-2 | 9/1-2 | 9/2-2 | 8 | 8 | 8/1-2 | 9/1-2 | 9 | 8/1-2 | 9 | 93.3 | 7.5 |
| PGR Solution + Derosal | 400 + 200 | 9/1-1 | 8/2-1.5 | 7/1-1 | 7/2-2 | 8 | 9/1-1 | 9 | 8 | 9/3-2 | 9 | 92.2 | 10.8 |
| PGR Solution + Ca + Deroral | 200 + 200 + 200 | 9/1-1 | 9/2-1.5 | 9 | 8/1-3 | 9/1-1 | 7/1 | 8 | 8/1-1 | 7/1-1 | 8 | 91.1 | 8.8 |
| PGR Solution + Ca + Derosal | 400 + 400 + 200 | 9/1-1 | 7/2-1 | 9 | 8 | 9/2-2 | 7/1-3 | 8/2-2.5 | 9/1-1 | 7/1-1 | 9/3-2 | 91.1 | 14.3 |

\* % of germination
\*\* % of diseased plants
The PGR Solution comprises an aqueous solution containing 0.015% IAA, 0.005% IBA, 0.009% cytokinin, 0.005% gibberellic acid, 1.000% emulsifier, 0.850% surfactant and 0.050% defoamer.
Calcium, when present, is used in a 10% aqueous solution.
Derosal is a trademark of Bayer Crop Service. Derosal comprises an aqueous solution of carbendazim and thiram.
x/y-z (x = number of plants, y = number of plants with symptoms and z = disease severity)
Scale of severity
1 = very severe symptoms or dead plants
2 = moderate symptoms (wilted plants)
3 = weak symptoms (initial wilt)

Observation of the results reported in Tables I-V and illustrated in FIGS. 1-4 indicates that there is a significant improvement in resistance to *Rhizoctonia solani* infestation by the application of PGR solutions to manipulate the auxin level in the plant. Treatment with solutions containing only PGRs, principally IAA, as the active ingredient reduces the percentage of diseased plants from 15.7 percent to 7.2-9.4 percent after seven (7) days. See FIG. 4 and the last column of Table IV. Treatment with solutions containing PGRs, together with calcium, show reductions from 15.7 percent to 5.7-7.2 percent. Derosal, a fungicide commonly used to treat *Rhizoctonia solani*, reduced the percentage of infestation from 15.7 percent to 5 percent. Thus, while the addition of PGRs, principally IAA, produced significant reduction in fungus infestation, it does not appear to be as good as Derosal. However, the PGRs do not have the negative environmental impact of such commercial fungicides.

Similarly, treatment with auxin-containing solutions reduced the percentage of plants infested with *Rhizoctonia solani* from 26.3 percent to 15.2-18.2 percent. Treatment with both PGRs and calcium resulted in further reduction in infestation levels to 12.0-13.2 percent after thirteen (13) days. See Table V. These levels compared quite favorably to that achieved by using Derosal wherein the infestation level was reduced to 11.2 percent. In general, treatment of dry bean seeds prior to planting with a solution containing PGRs, principally IAA, reduced the infection of the resulting plants with *Rhizoctonia solani* by approximately 50% from that observed with the controls. Addition of calcium resulted in further disease suppression.

The culture medium was removed by a wash with 20 ml of distilled water. Fungus micelles retained on the filter paper were dried in an oven at 40° C. for 3 hours. After equilibration to room temperature the dried micelles were weighed. Comparisons were made on the basis of dry weight. The results are reported below in Table VI.

TABLE VI

EFFECT OF SINGLE AND SEQUENTIAL APPLICATION OF AUXIN-CONTAINING SOLUTION ON IN VITRO GROWTH OF *RHIZOCTONIA SOLANI*

| Treatments | Concentration (ppm) | Applications Number | Time | Weight of Colonies | Difference (%) |
|---|---|---|---|---|---|
| Control (water) | 500 | 1 | In incubation | 77.1 | |
| PGR Solution | 100 | 1 | In incubation | 56.5 | −27 |
| PGR Solution | 1,000 | 1 | In incubation | 54.5 | −29 |
| PGR Solution | 10,000 | 1 | In incubation | 50.5 | −35 |
| PGR Solution | 100 | 5 (×20 ppm) | In incubation + 12, 24, 36, And 48 HAI* | 48.6 | −37 |
| PGR Solution | 1,000 | 5 (×200 ppm) | In incubation + 12, 24, 36, and 48 HAI | 50.4 | −35 |
| PGR Solution | 10,000 | 5 (×2,000 ppm) | In incubation + 12, 24, 36, and 48 HAI | 32.1 | −58 |

*HAI = Hours after inclusion
General Information
The PGR solution used in this experiment comprises an aqueous solution containing 0.045% IAA, 0.005% IBA, 0.009% cytokinin, 0.005% gibberellic acid, 1.000% emulsifier, 0.850% surfactant and 0.050% defoamer.

Development of chemical or biological systemic acquired resistance (SAR) inducers may represent an interesting alternative for growers regarding plant disease management since they feature low contamination risk to the environment and permit selection of isolates within a population of pathogens due to their mode of action and absence of inherent toxicity. Although the ability to induce resistance in plants has been known for decades, its potentialities have only been demonstrated recently. The following is an interesting example of in vitro inhibition of the growth of *Rhizoctonia solani*.

EXAMPLE 2

In this example, the effect of application of PGRs, principally indole-3-acetic acid (IAA), on the in vitro development of a soil fungus causing root rot in bean cultures, *Rhizoctonia solani*, was studied. Assessment of in vitro fungitoxic action of an auxin-containing solution on the *Rhizoctonia solani* fungus was undertaken for both single and sequential applications of PGR solutions.

A liquid culture medium (potato dextrose) was inoculated with 0.6 cm diameter discs of *Rhizoctonia solani*. Incubation conditions were maintained as 25° C. with a photoperiod of 12 hours under constant agitation. Total incubation time was 60 hours. Growth of the inoculum was observed at 12 hour intervals. Each test was replicated in triplicate.

Single and sequential applications of an auxin-containing solution were studied. In the sequential tests, five (5) applications were made commencing with incubation and continuing at 12 hour intervals thereafter. In the single application, the full dose of PGRs, principally IAA, was applied at incubation. The total quantity of PGRs applied in the five (5) applications equaled that of the corresponding single application.

After 60 hours of incubation, the liquid medium containing the culture medium, the PGR solution (or water control) and fungus micelles was filtered. A funnel containing weighed filter paper was connected to a kitassato with a vacuum pump.

As can be seen from the results reported in Table VI, application of the auxin-containing solution in all tested concentrations inhibited development of the *Rhizoctonia solani* fungus. Whether applied in a single dose or in five sequential doses, there was a significant reduction in fungus growth. While sequential application appeared to be more effective, producing higher reduction in fungal growth, a single application at the time of incubation reduced fungus growth by 27-35 percent. When applied sequentially in five increments separated by 12 hour intervals, fungus growth was reduced by 37-58 percent. Thus, it would appear that sequential application of lower doses of PGRs may prove most beneficial.

EXAMPLE 3

In further experiments, the effect of PGRs, principally IAA, on thrips was examined. Whenever conditions are hot and dry, thrips, and more particularly their nymphs attack onions. It is the nymphs, rather than the thrips, that do most of the damage. There is no effective chemical control for the problem. In a controlled field experiment an aqueous solution containing PGRs, principally IAA, was applied to onions. Two different tests were conducted. In each test, growing onion plants were sprayed with an aqueous solution containing 0.015% IAA, 0.005% IBA, 0.009% cytokinin and 0.005% gibberellic acid at the rate of 12 oz per acre. The areas were enclosed with netting so that none of the thrips could move from one treatment zone to another. Untreated controls were sprayed with water. Seven days (test 1) and eight days (test 2) after application of the auxin-containing solution, the number of thrips (*Thrips tabaci*), both adult and larvae, were observed and counted. The results are shown below in Table VII. This single treatment with PGRs resulted in a decrease of about 50% in the total number of thrips. Most importantly, the number of larvae which do most of the damage were decreased by more than 50 percent.

TABLE VII

REDUCTION OF ONION INFESTATION BY (*THRIPS TABACI*)
AFTER SINGLE TREATMENT WITH AUXIN-CONTAINING SOLUTION

| | Test 1 THRIPS (counted after 7 days) | | | Test 2 THRIPS (counted after 8 days) | | |
|---|---|---|---|---|---|---|
| | LARVAE | ADULT | TOTAL | LARVAE | ADULT | TOTAL |
| Control (untreated) | 53.9 ± 4.3 | 7.1 ± 0.7 | 61.0 ± 4.7 | 87.7 ± 15.2 | 4.7 ± 0.8 | 92.4 ± 15.5 |
| Treated with Auxin solution (12 oz/acre) | 21.8 ± 2.4 | 3.4 ± 0.4 | 25.2 ± 2.6 | 40.1 ± 7.9 | 3.3 ± 0.9 | 43.4 ± 8.2 |
| F | 42.82 | 20.15 | 44.84 | 7.71 | 1.35 | 7.81 |
| P | <0.0001 | <0.0001 | <0.0001 | 0.0124 | 0.2596 | 0.0120 |

General Information
The auxin solution used in this experiment comprises an aqueous solution containing 0.015% IAA, 0.005% IBA, 0.009% cytokinin, 0.005% gibberellic acid, 1.000% emulsifier, 0.850% surfactant and 0.050% defoamer.
F is the variance ratio (error sum of squares), while P is the probability measure (confidence level). With P < 0.0001, there is a 99.99% chance that the observed results are significant.

EXAMPLE 4

In a further experiment, the effect of PGRs on two-spotted spider mites (*Tetranychus urticae*) was examined on melons. A total of twenty (20) melon plants were used for this experiment. Ten (10) plants were treated with a solution containing auxin, while ten (10) were untreated to serve as controls. Growing melon plants were sprayed with an aqueous solution containing 0.015% IAA, 0.005% IBA, 0.009% cytokinin and 0.005% gibberellic acid at the rate of 12 oz per acre. Untreated controls were sprayed with water. A tractor-mounted sprayer operated at 70 psi and 32 gpa and configured with three TX7 hollow cone nozzles per row (1 on top and 2 on drops) was used to complete the spraying. The number of spider mites (both live and dead), including adult, immature and eggs, were observed and counted on 10 cm$^2$ disks (5 cm$^2$ from each of the top and bottom of the leaf) prior to treatment. Five (5) days after application of the IAA and control solutions, one leaf from each plant was sampled and the mites counted as above. The results are shown below in Table VIII. Prior to treatment there were on average 3.14±0.78 live mites per 4 cm$^2$ with substantially no dead mites. After treatment live mites had been reduced to only 0.58±0.26 per 4 cm$^2$. Further, after treatment 57.76±10.51 percent of the observed mites were dead. In contrast, for the controls there were still on average 1.54±0.27 live mites per 4 cm$^2$ with only 21.64±6.39 percent of the observed mites being dead.

TABLE VIII

REDUCTION IN INFESTATION OF MELONS BY TWO-SPOTTED SPIDER MITES (*TETRANYCHUS URTICAE*) AFTER SINGLE TREATMENT WITH AUXIN-CONTAINING SOLUTION

| | No. Mites per 4 cm$^2$ | | |
|---|---|---|---|
| | No. Live Mites | No. Dead Mites | Percent Dead Mites |
| Prior to Treatment | 3.14 ± 0.78 | 0.02 ± 0.02 | 0.04 ± 0.04 |
| 5 Days after Treatment | 0.59 ± 0.26 | 0.24 ± 0.07 | 56.76 ± 10.51 |
| 5 Days later with NO Treatment | 1.54 ± 0.27 | 1.22 ± 0.24 | 21.64 ± 6.39 |
| F | 3.42 | 3.21 | 9.20 |
| P | 0.0659 | 0.0749 | 0.0036 |

General Information
The auxin solution used in this experiment comprises an aqueous solution containing 0.015% IAA, 0.005% IBA, 0.009% cytokinin, 0.005% gibberellic acid, 1.000% emulsifier, 0.850% surfactant and 0.050% defoamer.
F is the variance ratio (error sum of squares), while P is the probability measure (confidence level). With P < 0.0001, there is a 99.99% chance that the observed results are significant.

EXAMPLE 5

In another experiment, the effect of IAA on two-spotted spider mites (*Tetranychus urticae*) was examined on eggplants. A total of twenty (20) eggplants were used for this experiment. Ten (10) plants were treated with a solution containing auxin, while ten (10) were untreated to serve as controls. Growing eggplants were sprayed with an aqueous solution containing 0.015% IAA, 0.005% IBA, 0.009% cytokinin and 0.005% gibberellic acid, at the rate of 12 oz per acre. Untreated controls were sprayed with water. A tractor-mounted sprayer operated at 70 psi and 32 gpa and configured with three TX7 hollow cone nozzles per row (1 on top and 2 on drops) was used to complete the spraying. The number of spider mites (both live and dead), including adult, immature and eggs, were observed and counted on 10 cm$^2$ disks (5 cm$^2$ from each of the top and bottom of the leaf) prior to treatment. Seven (7) days after application of the IM and control solutions, one leaf from each plant was sampled and the mites counted as above. The results are shown below in Table IX. Prior to treatment there were on average 6.04±0.91 live mites per 4 cm$^2$ with no dead mites. After treatment live mites had been reduced to only 1.22±0.29 per 4 cm$^2$. Further, after treatment 59.02±6.84 percent of the observed mites were dead. In contrast, for the untreated controls there were still on average 5.93±0.54 live mites per 4 cm$^2$ with only 9.19±2.49 percent of the observed mites being dead.

TABLE IX

REDUCTION IN INFESTATION OF EGGPLANTS
BY TWO-SPOTTED SPIDER MITES
(*TETRANYCHUS URTICAE*) AFTER SINGLE
TREATMENT WITH AUXIN-CONTAINING SOLUTION

| | No. Mites per 4 $cm^2$ | | |
|---|---|---|---|
| | No. Live Mites | No. Dead Mites | % Dead Mites |
| Prior to Treatment | 6.04 ± 0.91 | 0.00 ± 0.00 | 0.00 ± 0.00 |
| 7 Days after Treatment | 1.22 ± 0.29 | 1.46 ± 0.26 | 59.02 ± 6.84 |
| 7 Days later with NO Treatment | 5.98 ± 0.54 | 0.64 ± 0.18 | 9.19 ± 2.49 |
| F | 61.03 | 6.70 | 56.86 |
| P | <0.0001 | <0.0001 | <0.0001 |

General Information
The auxin solution used in this experiment comprises an aqueous solution containing 0.015% IAA, 0.005% IBA, 0.009% cytokinin, 0.005% gibberellic acid, 1.000% emulsifier, 0.850% surfactant and 0.050% defoamer.
F is the variance ratio (error sum of squares), while P is the probability measure (confidence level). With P < 0.0001, there is a 99.99% chance that the observed results are significant.

EXAMPLE 6

In a final experiment, the effect of PGRs on turnip aphids (*Lipaphis erysimi*) was examined on cabbage plants. A total of twenty (20) cabbage plants were used for this experiment. Ten (10) plants were treated with a solution containing auxin, while ten (10) were untreated to serve as controls. Growing cabbage plants were sprayed with an aqueous solution containing 0.015% IAA, 0.005% IBA, 0.009% cytokinin and 0.005% gibberellic acid at the rate of 12 oz per acre. Untreated controls were sprayed with water. A hand-held sprayer was used. Prior to treatment and then seven (7) days after application of the IAA and control solutions, all leaves from the plants were checked for aphids. The results are shown below in Table X. Prior to treatment those were about 93.2±8.2 live aphids per plant with no dead aphids. After treatment live aphids had been essentially eliminated, being reduced to only 0.2±0.1 per plant. Further, after treatment 97.6±1.4 percent of the observed aphids were dead. In contrast, the aphids continued to thrive on the untreated plants and none appeared to be dead.

TABLE X

REDUCTION IN INFESTATION OF CABBAGE BY TURNIP
APHIDS (*LIPAPHIS ERYSIMI*) AFTER SINGLE TREATMENT
WITH AUXIN-CONTAINING SOLUTION

| | No. aphids | | |
|---|---|---|---|
| | No. Live Aphids | No. Dead Aphids | % Dead Aphids |
| Prior to Treatment | 93.2 ± 8.2 | 0.0 ± 0.0 | 0.0 ± 0.0 |
| 7 Days after Treatment | 0.2 ± 0.1 | 17.1 ± 1.7 | 97.6 ± 1.4 |
| 7 Days later with NO treatment | N/C | 0.0 ± 0.0 | 0.0 ± 0.0 |
| F | 127.67 | 104.94 | 5297.02 |
| P | <0.0001 | <0.0001 | <0.0001 |

General Information
The auxin solution used in this experiment comprises an aqueous solution containing 0.015% IAA, 0.005% IBA, 0.009% cytokinin, 0.005% gibberellic acid, 1.000% emulsifier, 0.850% surfactant and 0.050% defoamer.
N/C means that the number of live aphids was not counted. None of the aphids appeared to be dead.
F is the variance ratio (error sum of squares), while P is the probability measure (confidence level). With P < 0.0001, there is a 99.99% chance that the observed results are significant.

The foregoing description of the invention has been directed in primary part to particularly preferred embodiments in accord with the requirements of the Patent Statue and for purposes of explanation and illustration. It will be apparent, however, to those skilled in the art that many modifications and changes in the specifically described methods and compositions may be made without departing from the true scope and spirit of the invention. For example, while indole-3-acetic acid is the preferred auxin, synthetic auxins, specifically, indole-3-butyric acid, may be employed. Further, other plant growth regulators, particularly cytokinins or gibberellins, may be used to manipulate the auxin levels. Further, while preferred application rates have been presented, it is known that different plants species (and, in fact, different tissues within a given plant), disease organisms and insects all require different auxin levels. Thus, those skilled in the art may readily adjust the suggested application rates as required to inhibit the growth of any specific disease organism or insect on any particular plant species. Further, while Applicant has attempted to explain the reasons for the observed improvements in the resistance of plants to attack by disease and insects, Applicant does not wish to be held to the theory proposed, because that mechanism is not fully understood. Therefore, the invention is not restricted to the preferred embodiments described and illustrated herein, but covers all modifications which may fall within the scope of the following claims.

What is claimed is:

1. A method for increasing germination in dry bean seeds comprising the steps of:
    forming an aqueous plant growth regulating solution consisting of water and 0.015% indole-3-acetic acid, 0.005% indole-3-butyric acid, 0.009% cytokinin, and 0.005% gibberellic acid; and
    applying the aqueous plant growth regulating solution to the seeds of dry bean plants by spraying the aqueous solution onto the seeds at the rate of 200 ml of solution to 100 kg of seeds prior to planting.

2. The method of claim 1, further comprising the step of,
    applying an aqueous calcium solution consisting of 10% calcium to the seeds of the dry bean plants at the rate of 200 ml of aqueous calcium solution to 100 kg of seeds.

3. A method for decreasing the number of thrips and thrip larvae on onion plants, comprising the steps of:
    forming an aqueous plant growth regulating solution consisting of water and 0.015% indole-3-acetic acid, 0.005% indole-3-butyric acid, 0.009% cytokinin, and 0.005% gibberellic acid; and
    spraying the aqueous solution onto growing onion plants at the rate of 12 oz per acre.

4. A method for decreasing the number of adult spider mites, immature spider mites, and spider mite eggs on plants, comprising the steps of:
    forming an aqueous plant growth regulating solution consisting of water and 0.015% indole-3-acetic acid, 0.005% indole-3-butyric acid, 0.009% cytokinin, and 0.005% gibberellic acid; and
    spraying the aqueous solution onto growing plants at the rate of 12 oz per acre, wherein the number of adult spider mites, immature spider mites, and spider mite eggs on the plants decreases.

5. The method of claim 4, wherein the plants are melon plants.

6. The method of claim 4, wherein the plants are eggplant plants.

7. A method for decreasing the number of turnip aphids on cabbage plants, comprising the steps of:
    forming an aqueous plant growth regulating solution consisting of water and 0.015% indole-3-acetic acid, 0.005% indole-3-butyric acid, 0.009% cytokinin, and 0.005% gibberellic acid; and
    spraying the aqueous solution onto growing cabbage plants at the rate of 12 oz per acre.

\* \* \* \* \*